United States Patent
Bab

[11] Patent Number: 5,127,831
[45] Date of Patent: Jul. 7, 1992

[54] FLEXIBLE-END IRRIGATION PROBE

[76] Inventor: Itay Bab, 20 Hate'ena St. Karmei Yossef, Ayalon, Israel

[21] Appl. No.: 707,876

[22] Filed: Jun. 3, 1991

[51] Int. Cl.$^5$ .............................................. A61C 17/00
[52] U.S. Cl. ........................................ 433/80; 433/88
[58] Field of Search ...................... 433/80, 81, 86, 88, 433/142, 143

[56] References Cited

U.S. PATENT DOCUMENTS

| | | | |
|---|---|---|---|
| 2,016,597 | 10/1935 | Drake | 433/142 |
| 3,137,297 | 6/1964 | Maurer et al. | 433/80 |
| 3,164,153 | 1/1965 | Zorzi | 433/88 |
| 3,823,477 | 7/1974 | Hedrick | 433/86 |
| 4,026,025 | 5/1977 | Hunt | 433/80 |
| 4,236,889 | 12/1980 | Wright | 433/88 |
| 4,315,742 | 2/1982 | Nash et al. | 433/86 |
| 4,512,769 | 4/1985 | Koran et al. | 433/80 |
| 4,619,612 | 10/1986 | Weber et al. | 433/80 |
| 4,676,749 | 6/1987 | Mabille | 433/88 |
| 4,941,298 | 2/1990 | Fernwood et al. | 433/88 |
| 4,984,984 | 1/1991 | Esrock | 433/88 |
| 4,993,941 | 2/1991 | Maita et al. | 433/80 |
| 4,998,880 | 3/1991 | Nerli | 433/80 |
| 5,033,961 | 7/1991 | Kandler et al. | 433/80 |

Primary Examiner—Paul J. Hirsch
Attorney, Agent, or Firm—Lowe, Price, LeBlanc & Becker

[57] ABSTRACT

The present invention describes a hollow irrigation probe consisting of two parts: (i) a rigid, straight or bent, metal or plastic arm with a proximal connection hub such as a luer lock or luer connection or threaded hub or other connection element; (ii) a short, flexible, plastic distal end with a blunt tapered or round tip. Said flexible part is fixed to the arm by means such as chemical bonding, glue, welding or insert molding or plasma etching or mechanical lock. The probe lumen opens at the center of the tip or laterally at some distance from the tip. The probe according to the present invention constitutes the end of pumping devices reaching the patient's body engineered for the delivery of antibiotic-/antiseptic or other physiologic and medically compatible solutions. These devices include different manual and automatic syringes, spray injectors and mechanically/electrically driven pump systems. Said flexible end part is designed for the atraumatic penetration into the gingival sulcus/periodontal pockets. The rigid arm enforces the flexible end into the space between the gum and tooth. It is possible to design multiple are shapes (and sizes) to facilitate accessibility to various teeth and tooth aspects. The new probe according to said invention is designed for use by professional and nonprofessional personnel including patient self treatment.

11 Claims, 1 Drawing Sheet

FLEXIBLE-END IRRIGATION PROBE

BACKGROUND OF THE INVENTION

The present invention relates to a hollow periodontal irrigation probe device for the delivery of any antibiotic/antiseptic or other physiologic and medically compatible solutions into a periodontal pocket or the gingival sulcus.

PRIOR ART

The periodontal pocket is a pathologic space formed between the soft gum tissue and tooth root as a result of the destruction of the tooth supporting alveolar bone and periodontal ligament. This space opens to the oral cavity and is populated by pathogenic bacterial species (M. A. Listgarten, J. Periodontol. 47:1-18, 1976). These bacteria cause further destruction of the tooth attachment apparatus leading eventually to tooth loss. Thus, the aim of all curative and preventive periodontal treatments is to arrest the initiation and progression of tissue destruction by removal of the pathogenic flora. Removal of the pathogenic flora from the pockets cannot be achieved by conventional oral hygiene measures which have a limited subgingival effect (P. Kho, F. C. Smales, J. M. Hardie, J. Chin. Periodontol. 12:676-688, 1985). One approach to this problem, widely used over the last decades, has been surgical pocket elimination. This procedure is costly, often results in considerable pain and discomfort and in the long run is characterized by a limited success rate. In mammals, particularly dogs and cats, where periodontal disease is the number one cause of tooth loss (B. Colomery 3d P. Frost, Vet. Clin. North Am. Small Anim. Pract. 16:817-833, 1986) the treatment consists of periodical scaling of dental sulcus that involve general anaesthesia and incubation (S. M. Marretta, Semin. Vet. Med. DSurg. Small Anim. 2:230-240, 1987). Recently, evidence that control of periodontal disease can be achieved without pocket elimination has been established (S. P. Ramfjord, J. Am. Dent. Assoc. 114:37-40, 1987). One such nonsurgical approach is the local administration into the pocket of antibiotics and antiseptics alone or in combination with mechanical debridement of the pocket. The simplest technique for such administration is repeated subgingival irrigation using the respective solutions. This is done using a delivery device equipped with a conventional blunt, rigid, metal needle (L. L. Soh, H. N. Newman, J. D. Strahan, J. Clin. Periodontal. 9:66-74, 1982; J. G. L. Khoo, H. N. Newman, J. Periodont. Res. 18:607-619, 1983). With this type of needle the device is operated effectively only by trained personnel. To avoid the risk of traumatizing the soft tissue pocket wall and epithelial attachment as well as the discomfort involved in tooth sensitivity resulting from the contact of the root with metal, the self-administered (by the patient) use is limited to buccal aspects of single-rooted teeth which constitute relatively accessible sites (L. Braatz, S. Garret, N. Claffey, J. Egelberg, J. Clin. Periodontol. 12:630-638, 1985). This limitation on patient-administered irrigation of antibacterial solutions results from needle rigidity and associated traumatizing potential as well as the use of only one form of bending. It is rather surprising that an atraumatic probe with a non metallic end of appropriate shapes and dimensions, it is not yet known for the purpose of subgingival irrigation in men and small animals (mammals).

BRIEF DESCRIPTION OF THE INVENTION

The present invention relates to a hollow periodontal irrigation probe device for the delivery of any physiologic and/or medical solution into a periodontal pocket comprising a rigid arm with a proximal connection hub, and a short flexible plastic distal end with a blunt tapered or round tip wherein said flexible-end is fixed to the rigid arm and wherein the probe lumen opens at the center of the tip or laterally at some distance from the tip.

DETAILED DESCRIPTION OF THE DRAWINGS

Figure 1A:
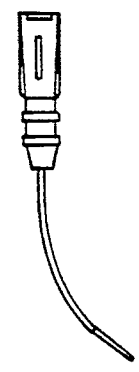
FIG. 1 illustrates examples of flexible-end periodontal irrigation probes according to the present invention.
Figure 1B:
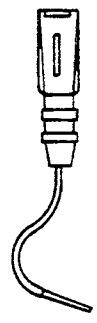
Figure 1C:
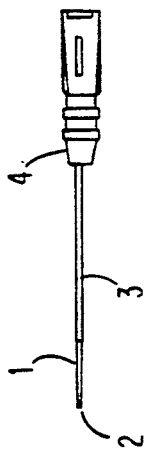

FIG. 1a, 1b and 1c, are side views of the device according to said invention.

FIG. 1a illustrates a device with a straight probe.

FIG. 1b and 1c illustrates a device with bent probes. The short flexible plastic distal end (1) with a blunt tapered or round tip (2) is fixed to the rigid metal or plastic arm (3) with a proximal connection hub (4).

Figure 2:
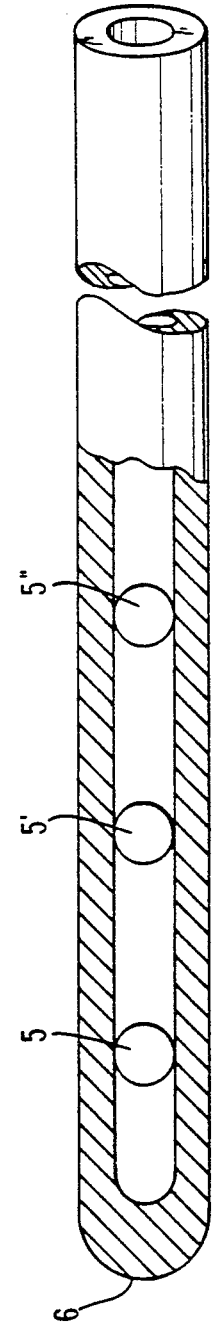
FIG. 2 illustrates a longitudinal section of the flexible end.

FIG. 2 illustrates the longitudinal section of the flexible end wherein the probe lumen opens laterally as multiple holes (5) ($t^i$) ($5^{ii}$) 2-6 mm proximal to the tip (6).

Figure 3:
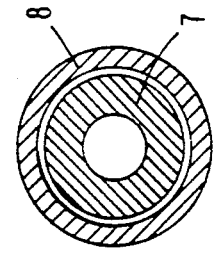
FIG. 3 illustrates a cross-section of the probe according to the invention at the point at which the flexible end is inserted to the rigid arm.

FIG. 3 illustrates a cross-section of the device according to the present invention wherein the flexible tip tube (7) is inserted into the rigid arm (8).

DETAILED DESCRIPTION OF THE INVENTION

The present invention describes a hollow irrigation probe consisting of two parts: (i) a rigid, straight or bent, metal or plastic arm with a proximal connection hub such as a luer lock or luer connection or threaded hub or other connection element; (ii) a short, flexible, plastic distal end with a blunt tapered or round tip. Said flexible part is fixed to the arm by means such as chemical bonding, glue, welding, insert molding or plasma etching or a mechanical lock. The probe lumen opens at the center of the tip or laterally at some distance from the tip. The probe according to the present invention constitutes the delivery end of pumping devices reaching the patient's body engineered for the delivery of antibiotic/antiseptic or other physiologic and medically compatible solutions. These devices include different manual and automatic syringes, spray injectors and mechanically/electrically driven pump systems. The flexible-end part is designed for the atraumatic non sensitizing penetration into the gingival sulcus/periodontal pockets. The rigid arm enforces the flexible end into the space between the gum and tooth. It is possible to design multiple arm shapes (and sizes) to facilitate accessibility to various teeth and tooth aspects. The new probe according to said invention is designed for use by professional and nonprofessional personnel including patient self treatment.

The flexible-end periodontal irrigation probe is a hollow device consisting of a 20-150 mm long rigid arm and 2-8 mm long flexible distal end part. A connection part such as a luer lock or luer connection or threaded hub or other connection element constitutes the proximal arm end. The arm is straight or bent as illustrated in FIG. 1. The arm is made of either metallic or a rigid plastic material. The distal end is made of flexible or semi-flexible nylon or polyethylene or copolymer or polypropylene or PVC or teflon or polyamide or any other suitable plastic material, with a degree of hardness of Shore A 55-100. The proximal hub is made of stainless steel or aluminum or polypropylene or polyethylene or any other suitable plastic material. The arm inner diameter is 14-25 gauge. The flexible end external diameter is 18-27 gauge. Depending on the combination of materials, fixation of the flexible end to the arm is achieved by insertion of an extended end tube through the arm and hub (using the arm as a sleeve) (FIG. 1) and immobilizing it by means such as an adhesive, chemical bonding, plasma etching, welding, insert molding or mechanical lock. Alternatively, similar means can be used for the connection of the flexible end tube to the distal end of the arm, thus joining together the lumens of the rigid arm and flexible end. The short flexible plastic distal end can be replaced and the new flexible end can be fitted and inserted to the rigid arm and then fixed to the rigid arm by any conventional mechanical lock. The flexible end has a blunt, rounded or tapered, atraumatic tip. The lumen opens at the center of the tip or laterally as a single hole or as multiple holes 2-6 mm proximal to the tip. The hole (holes) is (are) round, "fish eye" or any other form. In instances of multiple holes they will open to different directions at different distances from the tip.

The present invention also relates to a method for treatment of a pathologic space formed between the soft gum tissue and tooth root (a periodontal pocket) by using the device according to the invention wherein the rigid arm enforces the flexible end into the space between the gum and tooth and wherein a pumping device such as a manual or automatic syringe delivers antibiotic/antiseptic or other physiologic and medically compatible solutions to the periodontal pocket through the device according to the invention.

I claim:

1. A hollow periodontal irrigation probe device for the delivery of a physiologic and medical solution into a periodontal pocket in mammals and for irrigation of the interdental space, comprising a rigid arm with a proximal connection hub, and a short flexible plastic distal end with a blunt, tapered or round hollow tip, wherein said flexible end is fixed to the rigid arm and wherein the probe lumen opens at the center of the tip or laterally at a predetermined distance from the tip.

2. A hollow irrigation probe device according to claim 1, wherein the rigid arm is one of a metal or plastic arm.

3. A hollow irrigation probe device according to claim 1, wherein the proximal connection hub is one of a luer lock, luer connection on a threaded attachment.

4. A hollow irrigation probe device according to claim 1, wherein the short flexible plastic distal end is fixed to the rigid arm by one of chemical bonding, glue, welding, insert molding, plasma etching or mechanical locking.

5. A hollow irrigation probe device according to claim 1, further comprising mechanical lock means for detachably securing the short flexible plastic distal end to the rigid arm.

6. A hollow irrigation probe device according to claim 1, wherein the distal end is made of at least one of flexible or semi-flexible nylon, polyethylene, copolymer, polypropylene, polyvinyl chloride, teflon, or polyamide.

7. A hollow irrigation probe device according to claim 1, wherein the proximal hub is made of at least one of stainless steel, aluminum, polypropylene or polyethylene.

8. A hollow irrigation probe device according to claim 1, wherein said tip is an.

9. A hollow irrigation probe device according to claim 1, wherein said tip is an and wherein the lumen opens laterally as a single hole within the tip.

10. A hollow irrigation probe device according to claim 1, wherein said tip is an and wherein the lumen opens laterally in the tip as multiple holes open to different directions and at different distances from the tip.

11. A method for treatment of a pathologic space formed between the soft gum tissue and tooth root (a periodontal pocket) by using the device according to claim 1, comprising the steps of inserting the flexible end into the space between the gum and tooth, under the guiding action of the rigid arm and wherein a pumping device delivers antibiotic/antiseptic or other physiologic and medically compatible solutions to the periodontal pocket through said flexible end.

* * * * *

UNITED STATES PATENT AND TRADEMARK OFFICE
CERTIFICATE OF CORRECTION

PATENT NO. : 5,127,831
DATED : July 7, 1992
INVENTOR(S) : Itay BAB

It is certified that error appears in the above-indentified patent and that said Letters Patent is hereby corrected as shown below:

```
Column 1, line 36, change "incubation" to
--intubation--.
Column 4, line 31, after "an" insert --atraumatic tip--;
Column 4, line 33, after "an" insert --atraumatic tip--;
Column 4, line 36, after "an" insert --atraumatic tip--.
```

Signed and Sealed this

Twelfth Day of September, 1995

Attest:

BRUCE LEHMAN

*Attesting Officer*  *Commissioner of Patents and Trademarks*